United States Patent
Pedrazzini

(10) Patent No.: US 9,063,103 B2
(45) Date of Patent: Jun. 23, 2015

(54) CONVEYOR OF SPECIMEN CONTAINERS WITH SPUR UNITS IN LABORATORY AUTOMATION SYSTEMS

(75) Inventor: Gianandrea Pedrazzini, Paradiso (CH)

(73) Assignee: INPECO HOLDING LTD., Valletta (MT)

( * ) Notice: Subject to any disclaimer, the term of this patent is extended or adjusted under 35 U.S.C. 154(b) by 1118 days.

(21) Appl. No.: 12/445,001

(22) PCT Filed: Oct. 10, 2006

(86) PCT No.: PCT/EP2006/067241
§ 371 (c)(1),
(2), (4) Date: Jul. 27, 2009

(87) PCT Pub. No.: WO2008/043393
PCT Pub. Date: Apr. 17, 2008

(65) Prior Publication Data
US 2010/0034701 A1 Feb. 11, 2010

(51) Int. Cl.
*G01N 21/00* (2006.01)
*G01N 35/04* (2006.01)
*G01N 35/00* (2006.01)

(52) U.S. Cl.
CPC ...... *G01N 35/04* (2013.01); *G01N 2035/00326* (2013.01); *G01N 2035/0484* (2013.01)

(58) Field of Classification Search
CPC .............. G01N 35/04; G01N 35/0099; G01N 35/00732; G01N 2035/00801; G01N 2035/0465; G01N 2035/0406; G01N 2035/0467; G01N 2035/00782; G01N 2035/0093; G01N 2035/041; G01N 2035/0493; G01N 35/00603; G01N 35/0092; G01N 35/021; G01N 2035/00326; G01N 2035/0422; G01N 2035/0484; B01L 9/06; B01L 2300/021; B01L 3/5082; B01L 3/5453; B01L 9/50; B01L 9/02; F16C 29/005
USPC .................................. 422/50, 62–66, 401–405
See application file for complete search history.

(56) References Cited

U.S. PATENT DOCUMENTS

| | | | | |
|---|---|---|---|---|
| 4,699,767 | A | * | 10/1987 | Aihara .............................. 422/65 |
| 5,178,834 | A | * | 1/1993 | Kagayama et al. .............. 422/65 |
| 5,623,415 | A | * | 4/1997 | O'Bryan et al. ............... 700/225 |
| 5,998,754 | A | * | 12/1999 | Pervieux ........................ 209/587 |
| 6,019,945 | A | | 2/2000 | Ohishi et al. |
| 6,117,392 | A | | 9/2000 | Hanawa et al. |
| 6,520,313 | B1 | * | 2/2003 | Kaarakainen et al. ...... 198/369.5 |
| 6,522,976 | B2 | | 2/2003 | Shiba et al. |
| 8,211,381 | B2 | * | 7/2012 | Ricci et al. ..................... 422/404 |

* cited by examiner

*Primary Examiner* — Dean Kwak
(74) *Attorney, Agent, or Firm* — Birch, Stewart, Kolasch & Birch, LLP

(57) ABSTRACT

It is described a conveyor of specimen containers (9) supported by carriers (8) in laboratory automation systems comprising at least one analyzer (10, 50, 60). Said conveyor comprising a main transport unit (2), at least one spur transport unit (4-5, 7) allowing the positioning of the specimen container (9) inside said at least one analyzer (10, 50, 60) without removing said specimen container (9) from its carrier (8).

3 Claims, 9 Drawing Sheets

CONVEYOR OF SPECIMEN CONTAINERS WITH SPUR UNITS IN LABORATORY AUTOMATION SYSTEMS

The present invention concerns a conveyor of specimen containers with spur units in laboratory automation systems.

In the '90s Laboratory Automation concept started growing due to labour shortage, labour costs increase, awareness of the exposure of operators to biological hazard and so on.

It has been in above said years that institutions like the CLSI—Clinical and Laboratory Standard Institute (formerly NCCLS—National Committee for Clinical Laboratory Standards) started working on recommendations for the manufacturers of clinical instruments.

Some of said recommendations were related to indications on how a new analyzer should have sampled a specimen container: said indications are today known as "point in space" sampling.

Such recommendations were suggesting the position outside of the analyzer where the analyzer itself, with its own means, should have had to send the sampling probe in order to sample the specimen container.

Said indications were aimed to get all the analyzer's manufactures aligned to a standard to facilitate the design and realization of automatic processing systems for specimen containers.

Said automation solutions are generally obtained with different types of conveyor belts that move biological samples along a path where the laboratory process is performed: such a process may have different complexity including only part of the process tasks or may be very sophisticated and accomplish almost any task related with the laboratory process.

With analysers which are not CLSI compliant the only possible solution is presently represented by the use of complicated robotic arms and grippers capable to grip the specimen container out of the its carrier and transfer it into their sample feeding systems. This solution, generally known as "operator emulation solution", is very expensive, complicated and generally not feasible for small analyzers because of its cost.

As used herein, the term "specimen container" means a vessel that contains a solid or liquid and has a tubular opening for access to the contents, e.g., a test tube or vial.

As used herein the term "laboratory automation solution" means any system that has at least one analyzer integrated into the system; the system being capable to perform automatically the analytical portion of the process.

Within such laboratory automation solution the specimen containers are generally inserted into a carrier, which may (but it is not necessary) have a tag (transponder technology) to allow its identification along the process run and said carrier is moved along the process by a conveyor belt and it is stopped, as convenient, to execute automatically certain process task.

Object of the present invention is to provide a solution that allows all of the analyzers that are not CLSI compliant to be linked to a laboratory automation system that uses a conveyor system to move specimen containers along the pre-analytical, analytical and post-analytical process.

According to the invention said object is achieved by a conveyor of specimen containers supported by carriers in a laboratory automation system comprising at least one analyser, said conveyor comprising a main transport unit, characterized in that it further comprises at least one spur transport unit allowing the positioning of the specimen container inside said at least one analyzer without removing said specimen container from its carrier.

The spur transport unit allows to go inside the working area of the analyzer, stopping the carrier with the container in a sampling position of the analyzer.

The importance of this solution is due to the fact that most of the analyzers are still not compliant with the CLSI standards as their technology is still tight to technological constraints that are not facilitating the "point-in-space" sampling and this situation makes said analyzers almost excluded by the possibility of being linked to a laboratory automation solution.

The concept of the present solution has been obtained by reversing the idea that the analyzer should have had its own means in order to sample, outside of its foot print, accessing the specimen container that is presented on one side of the analyzer: the non obvious solution has been the concept of being able to use an accessory equipment to the conveyor system so to allow the specimen container to reach a position, inside the working area of the analyzer, where the regular pipetting tools of the analyzer can sample the specimen.

The characteristics and advantages of the present invention will appear evident from the following detailed description of an embodiment thereof illustrated as non-limiting example in the enclosed drawings, in which.

Figure 6:
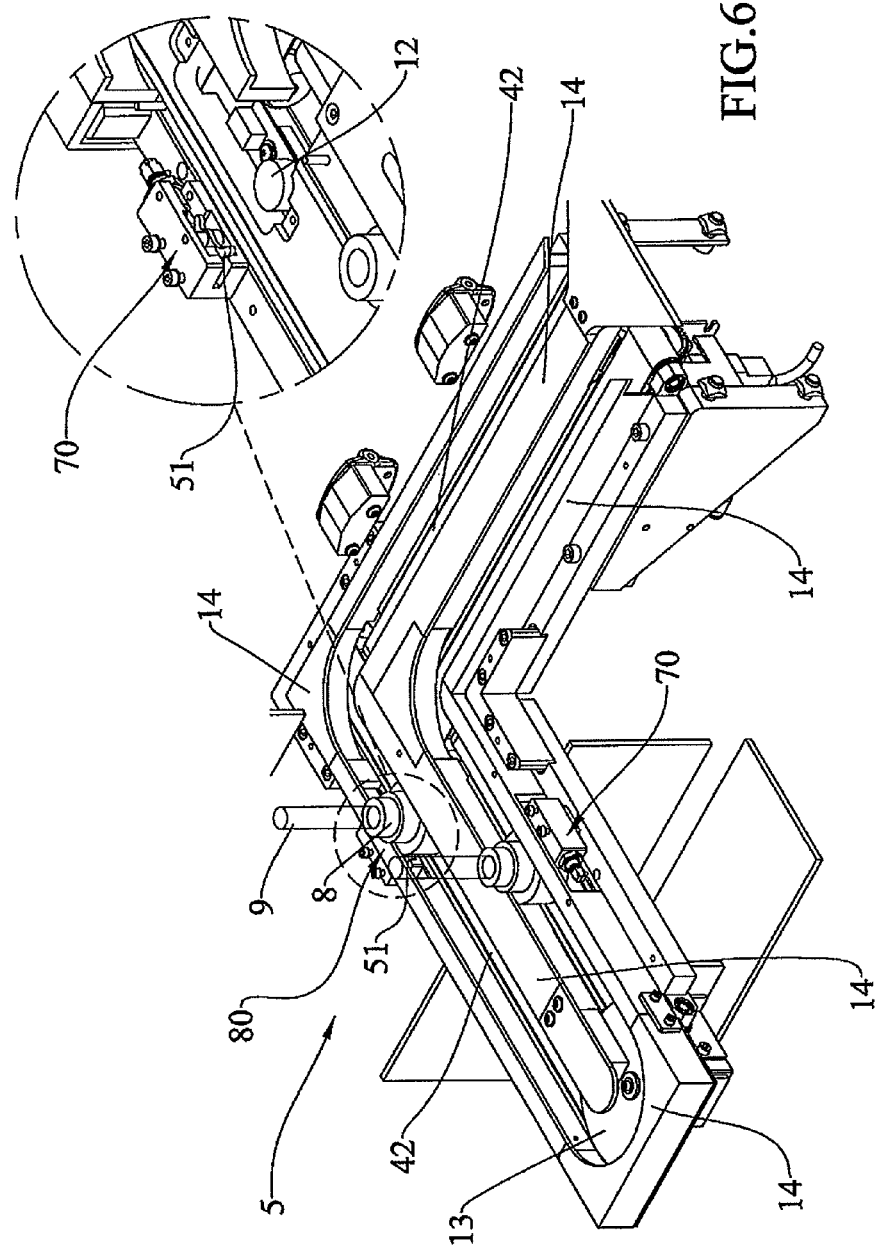
FIG. 6 is a perspective top view of a second embodiment of the spur unit.
Figure 7:
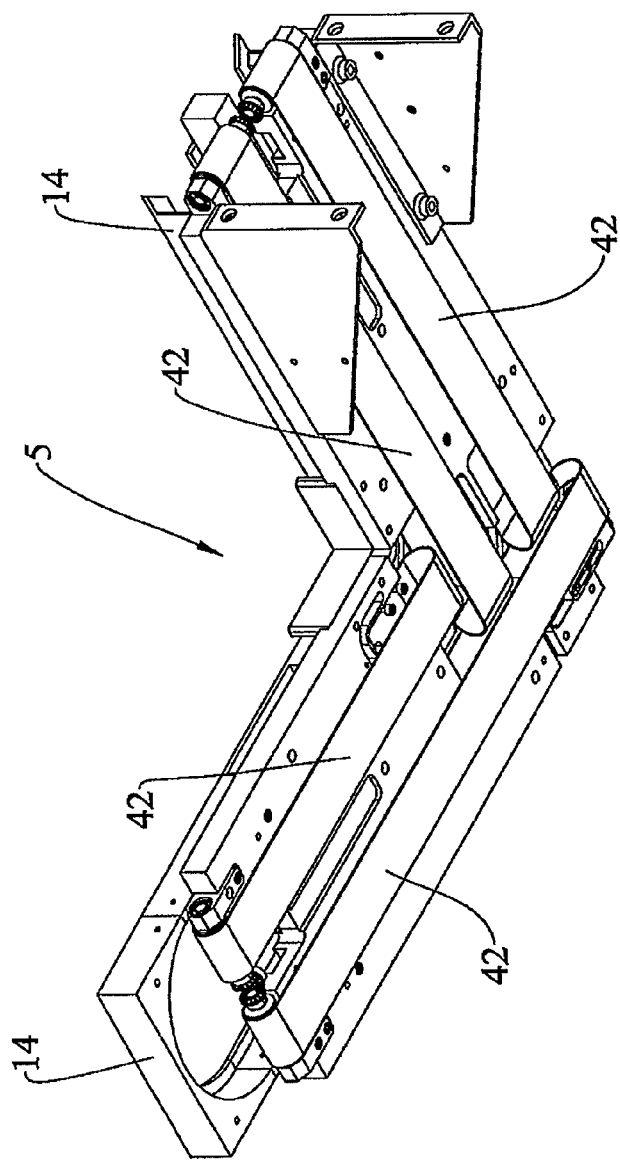
FIG. 7 is a perspective bottom view of said second embodiment of the spur unit.

A conveyor 1 shown in FIGS. 1-10 comprises a main transport unit 2 (FIG. 1) and spur transport units, in particular straight spur transport units 4 (FIGS. 2-5), disc spur transport units 7 (FIG. 8) and a "L" spur transport unit 5 (FIGS. 6-7).

Figure 1:
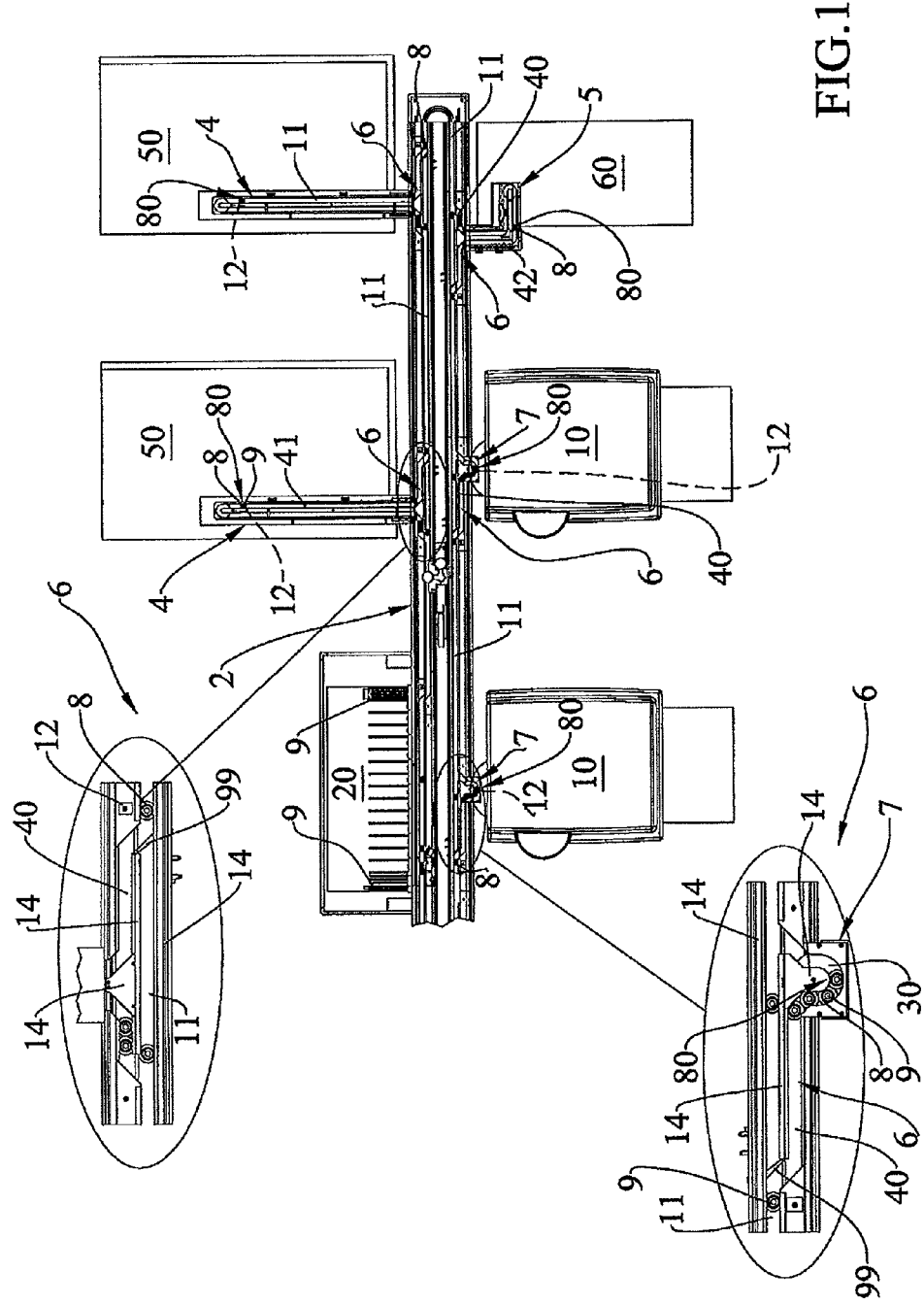
FIG. 1 is a top view of the conveyor according to the present invention.
Figure 2:
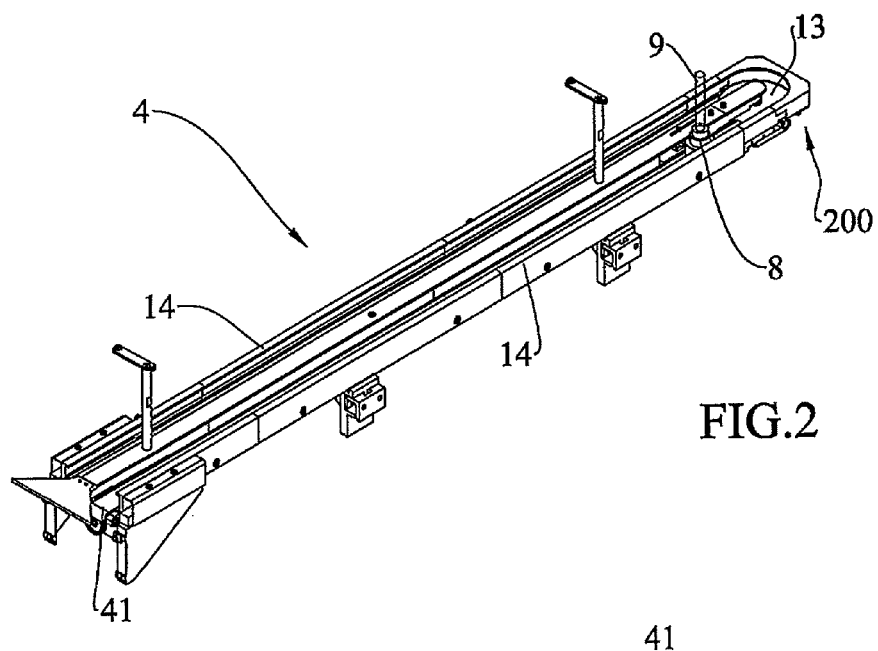
FIG. 2 is a perspective top view of a spur unit.
Figure 3:
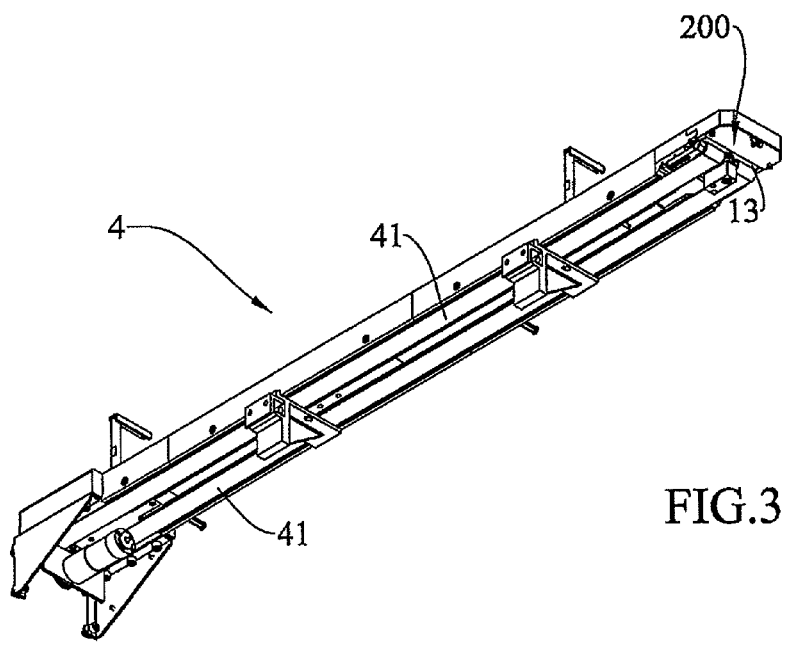
FIG. 3 is a perspective bottom view of a spur unit.
Figure 4:
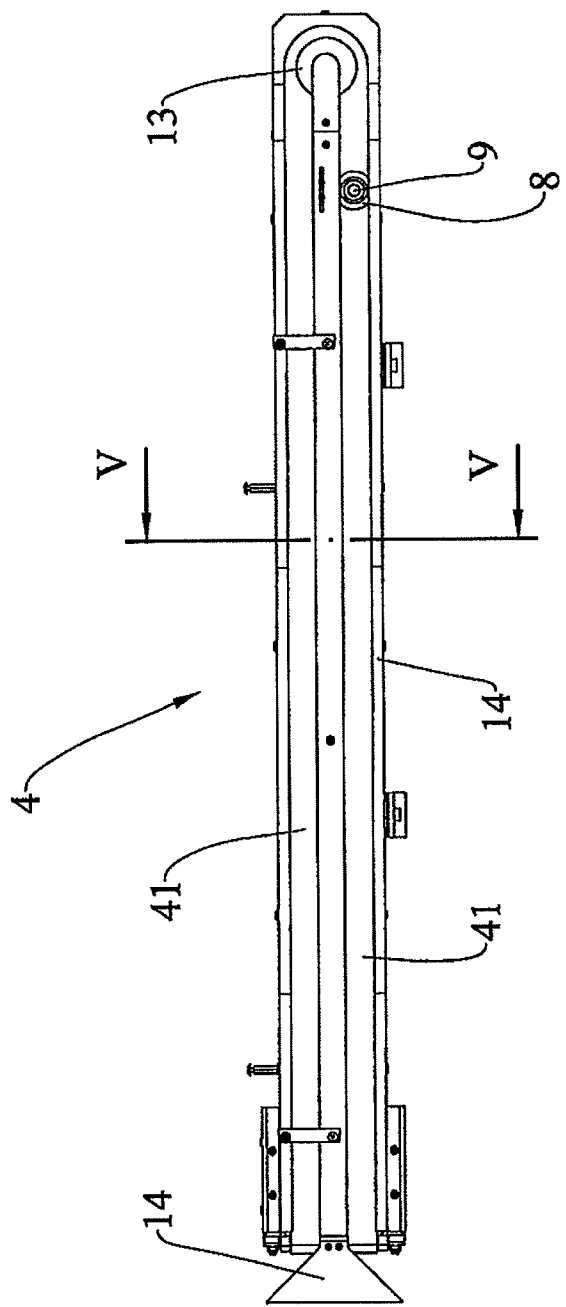
FIG. 4 is a top view of a spur unit.
Figure 5:
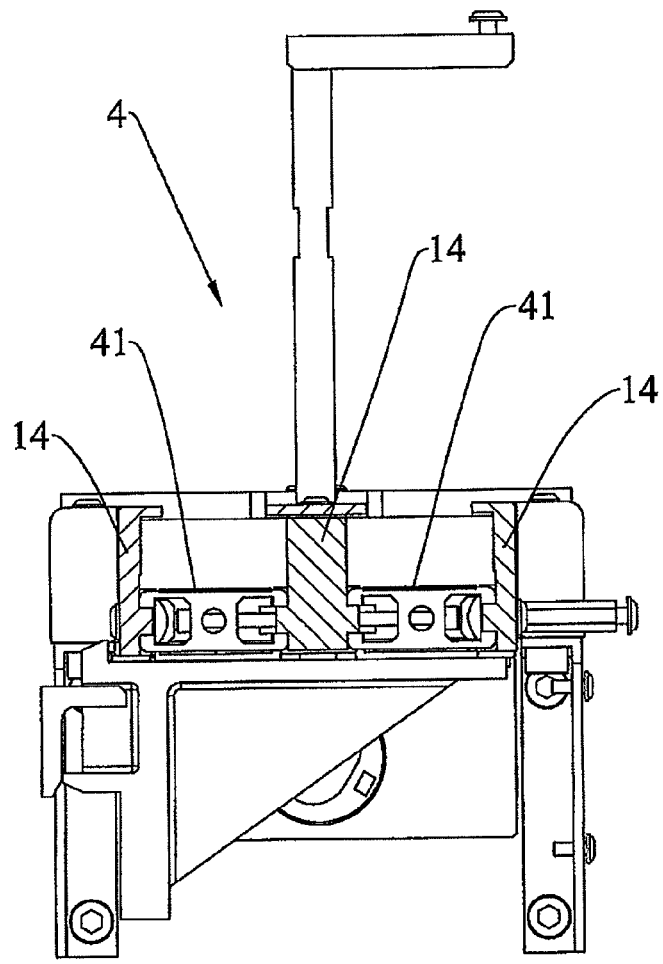
FIG. 5 is a sectional view according to line V-V of FIG. 4.

The spur transport units 4-5, 7 are connected with the main transport unit 2 through connecting portions or pit lanes 6 (FIG. 1).

On said conveyor 1, along guides 14, run, by main and secondary driven belts 11 and 40, detectable carriers 8 supporting specimen containers 9 which are processed in analyzers 10, 50, 60 placed inside a laboratory.

The laboratory also includes a container input/output module or rack with a loading/downloading arm (not shown).

The conveyor 1 supports detecting sensors 12 (FIGS. 6, 8), for example barcode detecting sensors, which control that a specimen container 9 remains associated with a certain carrier 8 for all the loop inside the laboratory.

In this way it is possible to identify the container 9 by its carrier 8.

The spur units 4-5 comprise container stop devices 70 and, in the end portions, reversing discs 13.

Figure 9:
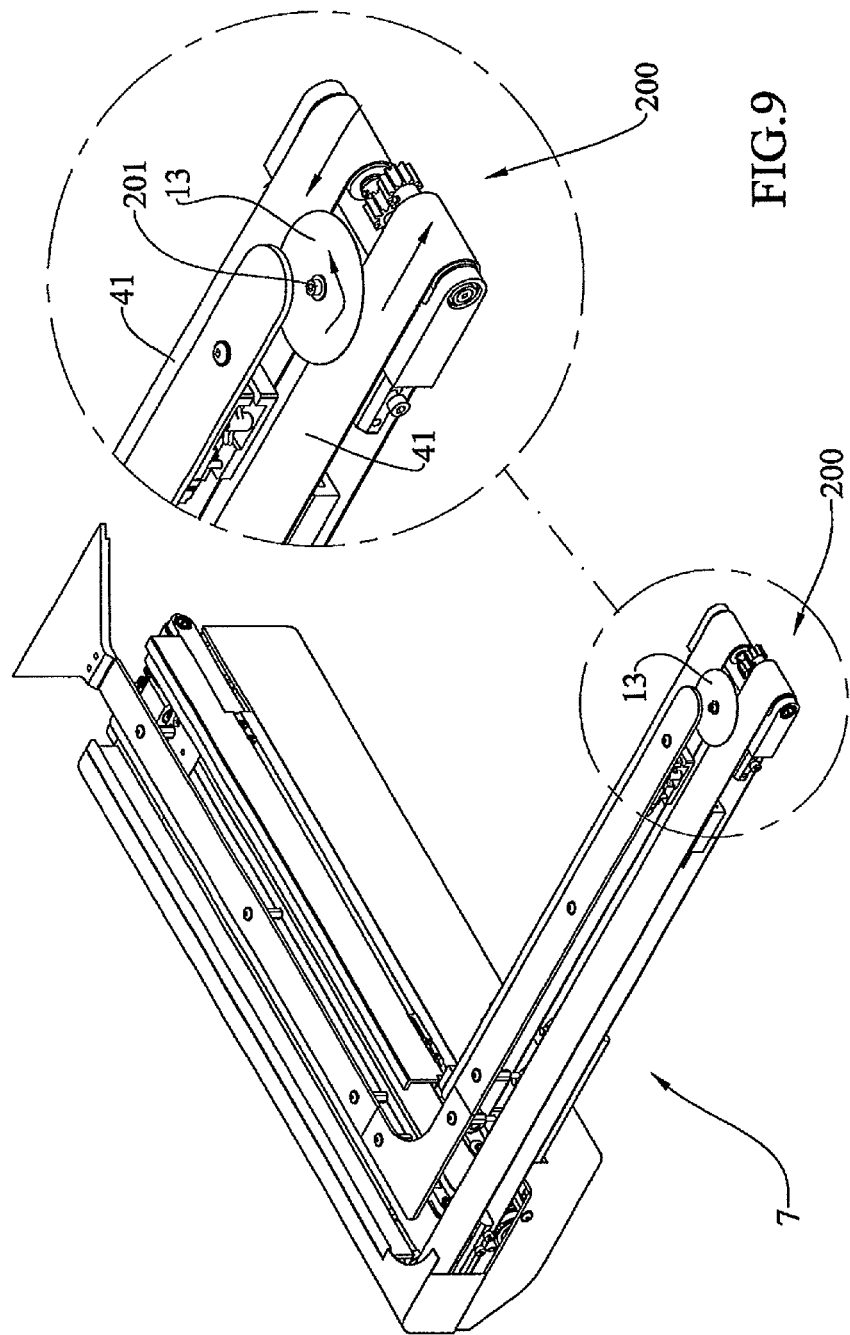
FIG. 9 is a perspective top view of a spur unit with an embodiment of a carrier reverse running device.
Figure 10:
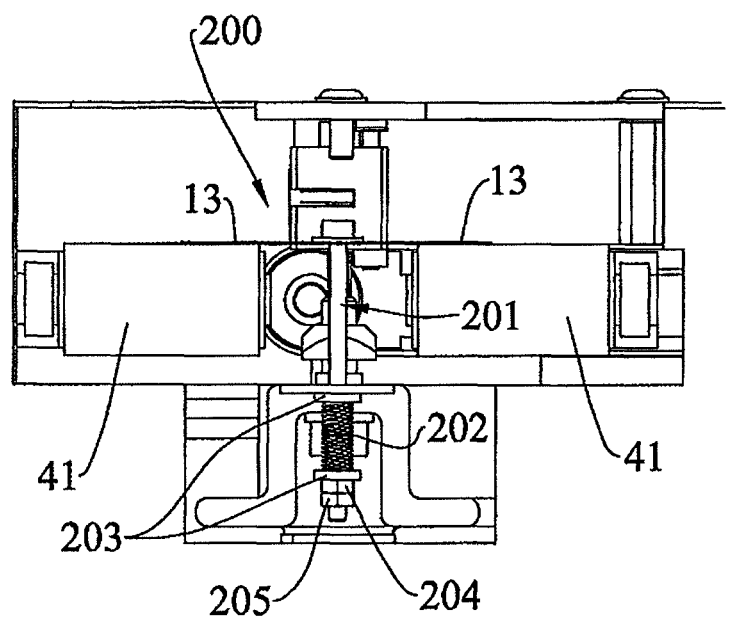
FIG. 10 is a frontal view of said embodiment of the carrier reverse running device.

In FIGS. 9 and 10 is shown an embodiment of a carrier reverse running device 200 which comprises a disc 13 mounted on a vertical screw shaft 201 with a traction spring 202 supported by bushes 203, with a nut 204 and a locknut 205.

The disc spur units 7 include further carrier stop devices 70 (FIGS. 6 and 8) and positioning discs 30.

Figure 8:
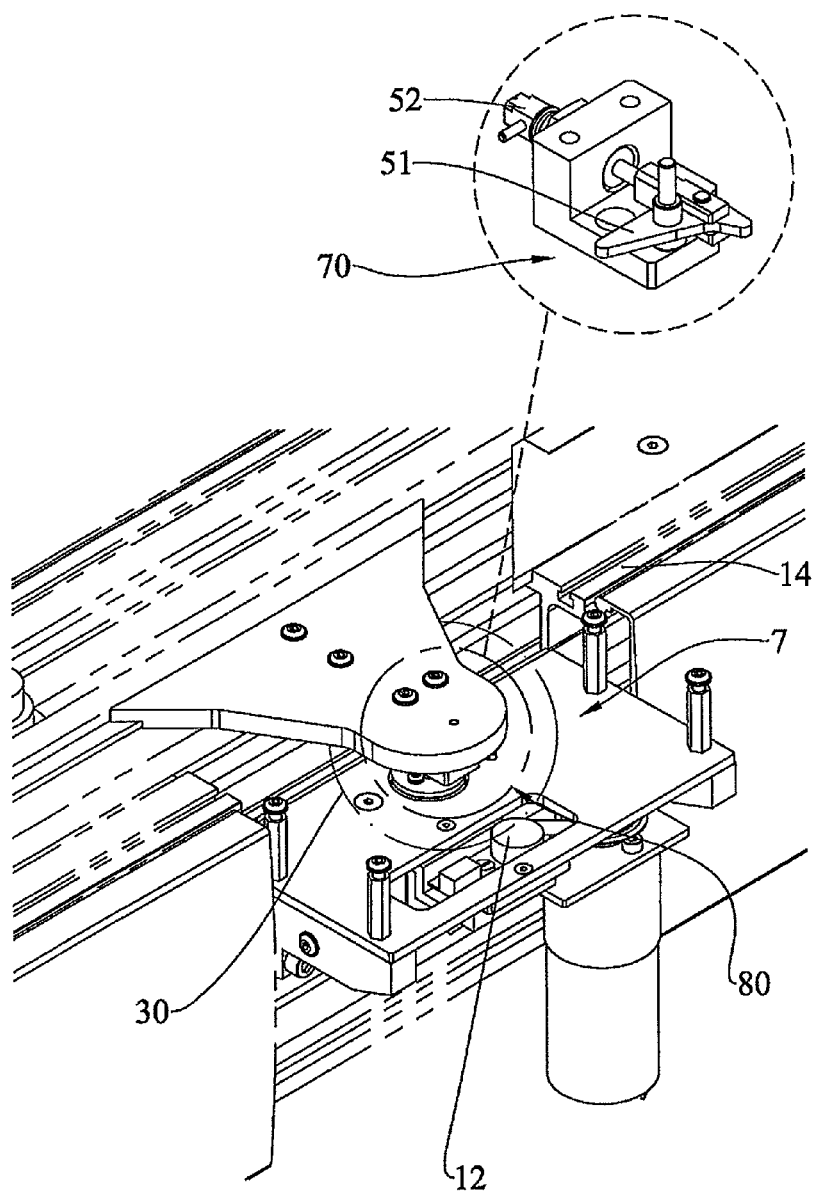
FIG. 8 is a perspective enlarged top view of a third embodiment of the spur unit.

An embodiment of carrier stopping devices 70 comprises a blocking member 51 driven by a pneumatic mechanism 52 (FIG. 8).

About the operation of the conveyor 1 according to the present invention, shown in FIG. 1, firstly a loading arm (not shown in the drawing) puts a specimen container 9 from a sample rack module 20 in a carrier 8. Detecting sensors 12 read the carrier 8 and a barcode reader (not shown) reads the specimen container 9.

Now a PC process controller or control unit knows that said container 9 is associated with said carrier 8.

Between two analyzers 10, 50, 60, the carriers 8 are moved by the main belt 11.

When a carrier 8 arrives inside or close to an analyzer 10, 50, 60, the controller, by the carrier ID sensors 12, decides if the container 9 supported by said carrier has to be processed by said analyzer 10, 50, 60.

There are three kinds of spurs according to the type of the analyzer 10, 50, 60 which might process the container 9:
1) a disc spur unit 7;
2) a straight spur unit 4;
3) a "L" spur unit 5.

In the first case, after carrier identification the carrier 8 is deviated by a diverting device 99 on a secondary belt 40 of the connecting portion or pit lane 6, which ships the carrier 8 on the driven positioning disc 30 of the disc spur unit 7. When the carrier 8 is in the sampling position 80 of the analyzer, the blocking member 51 stops the carrier 8 and the analyzer starts the sample pipetting operation.

In the second case, after carrier identification the carrier 8 is deviated by a diverting device 99 on a secondary belt 40 of the connecting portion or pit lane 6, which ships the carrier 8 on the driven belt 41 of the straight spur unit 4. When the carrier 8 is in the sampling position 80 of the analyzer, the blocking member 51 stops the carrier 8 and the analyzer starts the sample pipetting operation.

Finally, in the third case, after carrier identification the carrier 8 is deviated by a diverting device 99 on a secondary belt 40 of the connecting portion or pit lane 6, which ships the carrier 8 on the driven belt 42 of the "L" spur unit 4. When the carrier 8 is in the sampling position 80 of the analyzer, the blocking member 51 stops the carrier 8 and the analyzer starts the sample pipetting operation.

In the last two cases the sampling position 80 is inside the machine, in particular in the second case is depth inside the analyzer.

The choice of the type of spur unit 4-5, 7 depends on the arrangement of the analyzer.

According to the object of the present invention, the container 9 remains always on its carrier 8, so that the link between them is never broken.

When the pipetting is finished, the blocking member 51 disengages the carrier 8, the belts 41-42 and the carrier reverse running device 200 send the carrier 8 to the connecting portion or pit lane 6 and finally to the main belt 11.

In the carrier reverse running device 200 (FIGS. 9, 10), the rotation of the disc 13 is directly driven by the belt 41-42. A correct setting of the traction spring 202 allows to generate a friction between the upper surface of said belt 41-42 and the bottom surface of the disc 13, being the rotation of the disc due to the opposite verse of motion of the parallel adjacent belts 41-42.

Said reverse running device 200 is also usable in the main belt 11.

The container 9 is now ready for the next analyzer 10, 50, 60.

Usually in the laboratory there are further work stations, for example a decapper station, a desealer station or a capper station (not shown in the drawings).

When operations on a container 9 are finished, at the end of the conveyor loop, the container 9 is gripped by a downloading arm, separated from the carrier 8 and put in the rack 20.

The spur units (4-5, 7) allow flexibility inside a medical laboratory, depending the conveyor arrangement on the building of the analyzers.

The invention claimed is:

1. A conveyor for conveying a plurality of carriers, each carrier supporting single specimen containers in a laboratory automation system, said laboratory automation system containing analyzers, comprising:
   a main transport unit connected by connecting portions to spur transport units suitable to convey said carriers to sampling positions inside analyzers associated with one of said spur transport units, the spur transport units structurally separated from said analyzers, said main transport unit being provided with a main driving belt,
   each spur transport unit being provided with a going driven belt and a return driven belt disposed substantially parallel to each other,
   wherein each spur transport unit has different dimensions and each analyzer has a recess having dimensions corresponding to the dimensions of the spur transport unit associated with the analyzer,
   said connecting portions including an identifying device, a diverting device, a secondary belt disposed substantially parallel to said main driving belt, and a guide which ships carriers on the going driven belt of each spur transport unit not disposed parallel to said secondary belt,
   each spur transport unit allowing the positioning, by a blocking member actuated by the identifying device of the specimen container in the sampling position inside the analyzer, without removing the specimen container from a carrier, and
   each spur transport unit being provided with a reverse running device, including a friction disc interacting with said going driven belt and with said return driven belt to return the carriers supporting the analyzed containers back to the connecting portions and to the main transport driving belt.

2. The conveyor according to claim 1, wherein the reverse running device comprises a disc mounted on a vertical screw shaft with a vertical traction spring that creates friction between an upper surface of the going and return belts and a bottom surface of the disc due to the rotation of the disc and the opposite motion of the parallel, adjacent belts.

3. The conveyor according to claim 1, wherein the spur unit comprises a disc spur unit, a straight spur unit or an "L" spur unit.

* * * * *